United States Patent
Schaupp et al.

(10) Patent No.: US 7,022,071 B2
(45) Date of Patent: Apr. 4, 2006

(54) METHOD FOR MEASURING THE CONCENTRATION OF SUBSTANCES IN LIVING ORGANISMS USING MICRODIALYSIS AND A DEVICE FOR CARRYING OUT SAID METHOD

(76) Inventors: Lukas Schaupp, Peinlichgasse 6, Graz (AT) A-8010; Thomas Pieber, Medizinische Universitätsklinik, Auenbruggerplatz 15, Graz (AT) A-8036

( * ) Notice: Subject to any disclaimer, the term of this patent is extended or adjusted under 35 U.S.C. 154(b) by 17 days.

(21) Appl. No.: 10/482,845

(22) PCT Filed: Jul. 5, 2002

(86) PCT No.: PCT/AT02/00197

§ 371 (c)(1),
(2), (4) Date: Jan. 6, 2004

(87) PCT Pub. No.: WO03/003911

PCT Pub. Date: Jan. 16, 2003

(65) Prior Publication Data

US 2004/0168934 A1    Sep. 2, 2004

(30) Foreign Application Priority Data

Jul. 6, 2001    (AT) ............................. A 1057/2001

(51) Int. Cl.
*A61B 5/00* (2006.01)

(52) U.S. Cl. .................. 600/309; 600/322; 600/365
(58) Field of Classification Search ............... 600/309, 600/310, 322–328, 345–361, 364, 365; 604/4.01, 604/6.16, 5.01–5.04, 6.01–6.06, 6.09–6.11; 210/646, 647, 650, 739, 743, 745

See application file for complete search history.

(56) References Cited

U.S. PATENT DOCUMENTS

| 3,520,298 A | * | 7/1970 | Lange ......................... 604/29 |
| 3,881,483 A | * | 5/1975 | Sausse ...................... 604/6.14 |
| 3,960,689 A | * | 6/1976 | Lanier et al. ............... 204/435 |

(Continued)

FOREIGN PATENT DOCUMENTS

DE    197 15 440    8/1998

(Continued)

OTHER PUBLICATIONS

"Continuous Analyte Monitoring to Aid Clinical Practice" IEEE Engineering in Medicine and Biology Magazine, IEEE Inc. New York, US by Alcock S. J., et al. (Jun. 1994) (Intl. Srch. Rep.).

*Primary Examiner*—Max F. Hindenburg
*Assistant Examiner*—Patricia C. Mallari
(74) *Attorney, Agent, or Firm*—Collard & Roe, P.C.

(57) ABSTRACT

The invention relates to a method for measuring the concentration of substances in living organisms using microdialysis, whereby bodily fluid is mixed with a perfusate and passed through a membrane and a substance value is determined for the bodily fluid with the aid of a sensor unit. According to the invention, to allow for the limited transport through the membrane, so that the measured substance value differs from the actual substance value in the organism, a reference substance present in said organism with a known value is also measured after passing through the membrane and mixing with the perfusate and the actual substance value is determined, based on the quotient from the known reference substance value divided by the measured reference substance value, multiplied by the measured substance value.

12 Claims, 7 Drawing Sheets

U.S. PATENT DOCUMENTS

Figure 1:
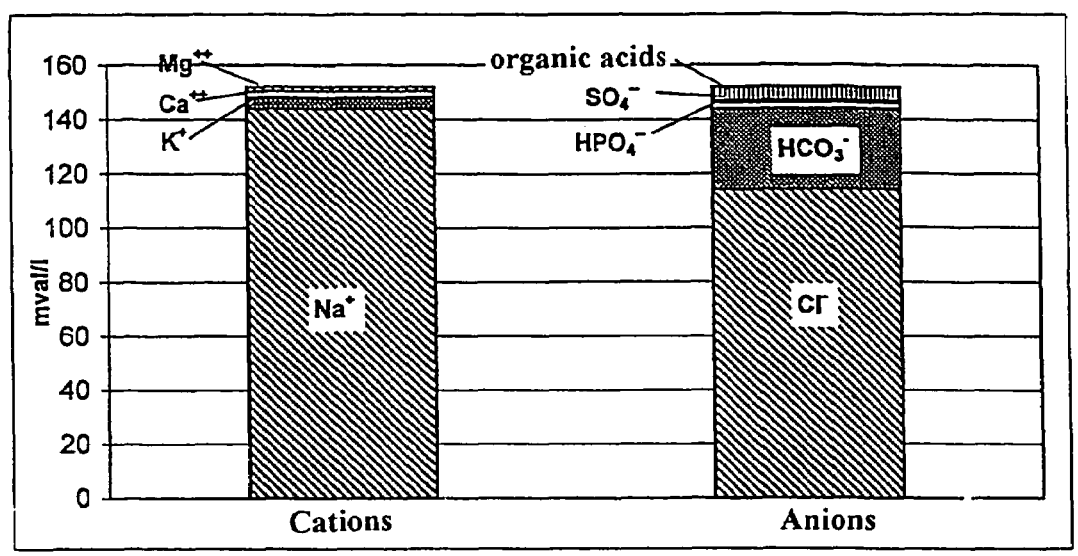

| | | | |
|---|---|---|---|
| 4,627,893 A * | 12/1986 | Cormier et al. | 205/779 |
| 4,694,832 A | 9/1987 | Ungerstedt | |
| 4,828,543 A * | 5/1989 | Weiss et al. | 604/6.09 |
| 5,002,054 A | 3/1991 | Ash et al. | |
| 5,097,834 A | 3/1992 | SkrabalFack | |
| 5,191,900 A | 3/1993 | Mishra | |
| 5,193,545 A | 3/1993 | Marsoner et al. | |
| 5,237,993 A * | 8/1993 | Skrabal | 600/309 |
| 5,298,022 A | 3/1994 | Bernardi | |
| 5,462,645 A | 10/1995 | Alberry et al. | |
| 5,954,643 A | 9/1999 | Van Antwerp et al. | |
| 6,463,312 B1 * | 10/2002 | Bergveld et al. | 600/345 |
| 6,852,500 B1 * | 2/2005 | Hoss et al. | 435/14 |

FOREIGN PATENT DOCUMENTS

| | | |
|---|---|---|
| EP | 300 008 | 3/1992 |
| EP | 1 072 222 | 1/2001 |
| GB | 2297383 | 7/1996 |
| WO | WO 93 05701 | 4/1993 |
| WO | WO 96/35369 | * 11/1996 |
| WO | WO96 35369 | 11/1996 |
| WO | WO 99 39629 | 8/1999 |
| WO | WO 99 45982 | 9/1999 |

* cited by examiner

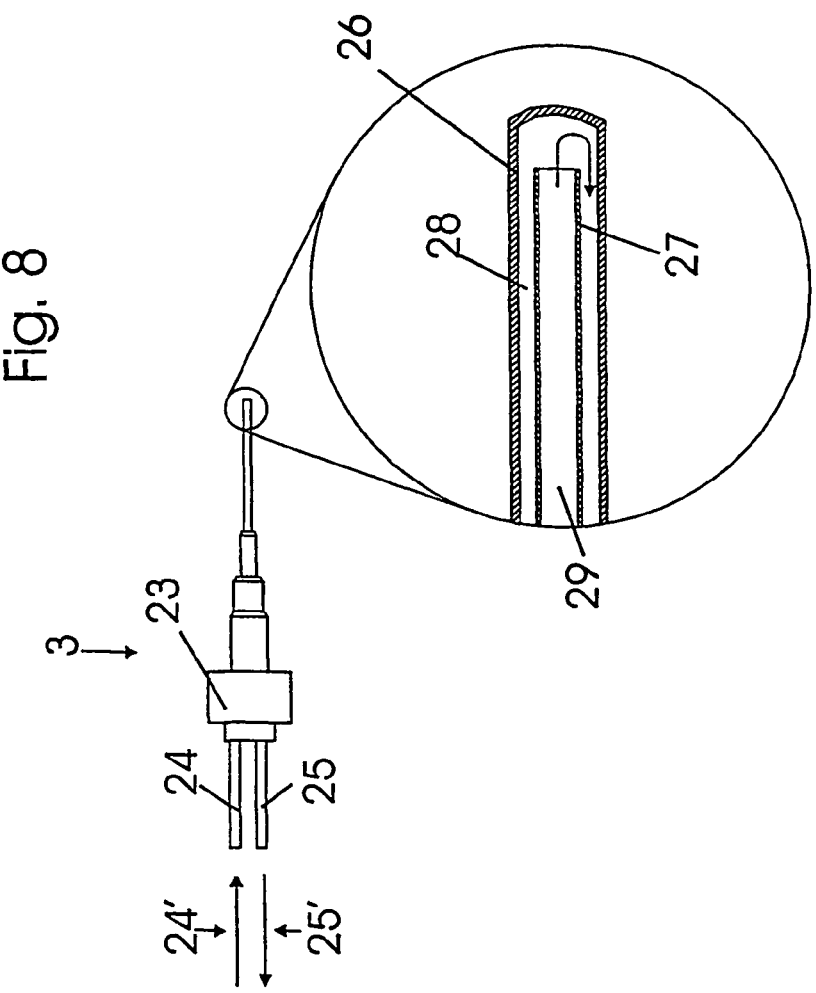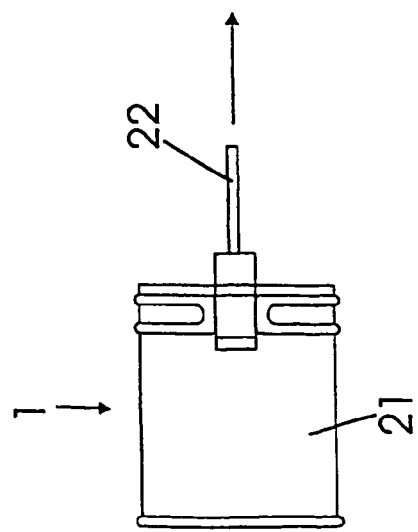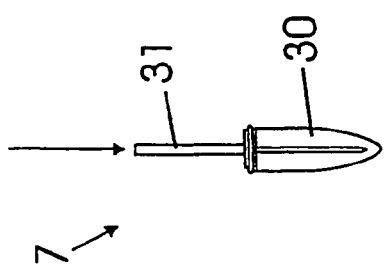

METHOD FOR MEASURING THE CONCENTRATION OF SUBSTANCES IN LIVING ORGANISMS USING MICRODIALYSIS AND A DEVICE FOR CARRYING OUT SAID METHOD

CROSS REFERENCE TO RELATED APPLICATIONS

Applicants claim priority under 35 U.S.C. §119 of Austrian Application No. A1057/2001 filed Jul. 6, 2001. Applicants also claim priority under 35 U.S.C. §365 of PCT/AT02/00197 filed Jul. 5, 2002. The international application under PCT article 21(2) was not published in English.

The invention relates to a method for measuring the concentration of substances in living organisms using microdialysis, wherein bodily fluid is mixed with a perfusate and passed through a membrane, and a substance value of the bodily fluid is determined using a sensor unit.

Furthermore, the invention relates to a device for carrying out this method.

In many areas of medicine or related areas of technology, it is frequently necessary to repeatedly or continuously measure concentrations or compositions of bodily fluids, e.g. in order to determine derailments from homeostasis and be able to treat them. For example, diabetes mellitus represents a derailment of the metabolism, where insulin is used to treat this. In this connection, however, late complications, such as premature blindness, heart and kidney failure, or neuropathy, cannot be avoided, rather they can only be delayed. One of the weak points in treatment and therefore a cause of the late consequences of this disease is certainly the fact that the coordination of insulin injections and blood glucose is not always optimal. In order to be able to adjust the insulin injections to the body's needs, the glucose concentration must first be determined. Therefore, continuous or constant measuring of the glucose concentration would be optimal for the correct insulin injections. In recent years, greater attention has been paid to quantification of the glucose in the tissue fluid, which has a close connection with the plasma glucose. Problems that occur in measurements in blood, such as coagulation, the risk of infection, protein stress, etc., are then at least greatly reduced.

In detail, different possibilities have already been proposed for continuously measuring the glucose or, very generally, for measuring substances in tissue fluid:

1. Minimally invasive sampling methods, such as microdialysis (see, for example, U.S. Pat. No. 5,191,900 A; U.S. Pat. No. 4,694,832 A), the open microperfusion technique (see, for example, EP 300 008 B, U.S. Pat. No. 5,193,545 A), or the ultrafiltration technique (see, for example, U.S. Pat. No. 5,002,054 A);

2. Sensors that are introduced directly into the tissue (see, for example, U.S. Pat. No. 5,954,643 A); or 3. Techniques by means of which the tissue fluid is collected through the skin (suction technique, inverse iontophoresis).

Microdialysis, to which the invention specifically relates, and the open microperfusion technique have in common perfusion of the catheter with a perfusate, which is mixed with the bodily fluid by way of open perforations in the case of the open microperfusion technique, whereas in the case of microdialysis, a fluid exchange takes place by way of a membrane. This membrane has the advantage that the exchange of molecules between the bodily fluid and the perfusate can be selectively controlled (size, shape, charge, etc. of the molecules), however these properties are changed over time, due to deposits of endogenous substances (predominantly proteins, but also cells). These deposits are accompanied by a change in the transport properties of the molecules by way of the membrane, and this is reflected by a reduced concentration of the molecules in the perfusate.

According to EP 300 008 B, these deposits are circumvented in that the hollow needle, which is structured as a subcutaneous needle/catheter, has an open exchange channel in the wall region, so that an open exchange can take place between the bodily fluid and the perfusate, i.e. this method belongs to the open microperfusion technique.

WO 96/35369 A1 describes a method for determining the production of certain bodily substances, in which calibration takes place by means of forming a quotient. In this connection, a calibration fluid is added to the substance to be examined, whereby the concentration and the amount of the calibration substance are known. With the prerequisite that the calibration fluid is not decomposed, the relative production rate of the substance to be examined can be determined, but the absolute concentration cannot.

DE 197 15 440 C1 describes a (similar) technique in which a conditioning and standard solution are supplied from an external source. Since no quantification of the substance to be determined is possible in this arrangement, comparisons are made, and the concentration of the substance to be determined can be established by means of extrapolation of the signals. The arrangement is particularly complicated since both the concentration and the flow-through velocity of the conditioning and standard solution must be modified.

EP 1 072 222 A2 describes a method and an arrangement for determining the concentration of glucose in a bodily fluid, in which a comparison is performed between a perfusate solution that has been externally supplied, and the concentration of the substance in the body. In this connection, different glucose concentrations are added to the perfusate from the outside. In addition to the complexity of the arrangement, the system is also particularly slow, since the external addition of glucose must always be adjusted to the body's own glucose concentration.

WO 93/05701 as well as GB 2 297 383 A relate to electrode arrangements that are housed in a microdialysis catheter. Here, the matter of concern is measuring the electrical conductivity, not measuring the concentration of a specific substance.

The invention now attempts to take advantage of the advantages of the membrane (sterile barrier, targeted exclusion of molecules, etc.) and, in this connection, to take into consideration the deposits on the membrane, whereby the invention tries to achieve quantification of the permeability of the membrane during the measurement.

It is accordingly a task of the invention to propose a method as well as a device as initially mentioned, in order to assure a reliable measurement of the concentration of the desired substance despite the use of a membrane in the course of the microdialysis technique and, at the same time, to utilize the advantages of the use of a membrane, such as the availability of a sterile barrier, the targeted exclusion or through-put of molecules, etc.

To accomplish this task, the invention provides a method as well as a device as defined in the independent claims.

Advantageous embodiments and further developments of the invention are characterized in the dependent claims.

Using the technique according to the invention, the advantages of using microdialysis, i.e. the use of a membrane, are combined with those of a precise determination of the concentration of the desired substances, because of the use of reference substances. In this connection, reference substances whose concentrations or properties in the tissue are known and constant are preferably used.

The equilibration (the exchange) between bodily fluid and perfusate is a function of the membrane exchange surface and the flow velocity of the perfusate. In the case of an infinitely small flow velocity, complete equilibration between the two fluids takes place. However, because of the slow flow velocity, there are two decisive disadvantages for measuring the substances in the perfusate: First, the amount of fluid obtained is very slight per time unit; and second, the delay becomes correspondingly great because of the hose length (system delay).

For this reason, a higher flow velocity is desired, in order to have more fluid available more rapidly. The disadvantage of this mode of operation consists of the fact that the two fluids are not completely mixed, which could be balanced out by means of measuring other parameters, thereby resulting in additional demands on the measuring technique, which proves to be a difficulty, in particular, in connection with on-line measurements. In order to be able to quantify the actual recovery rate and thereby the concentration outside of the catheter, different calibration methods for sampling techniques have been proposed: The simplest method consists of determining the recovery rate in vitro. The values measured in vivo are then corrected, using this found rate. It was possible to show, in many instances, not only that the recovery rate in vitro and in vivo differ, but also that the recovery rate in vivo changes.

Another method for determining the recovery rate consists of a change in the flow velocity and a related change in the recovery rate. If the functional connection between the recovery rate and the flow velocity is known, a calculation back to the concentration outside the catheter can be made (this determination of the recovery rate is called "zero flow rate" protocol in the literature, because complete mixing between the fluid outside the catheter and the perfusate takes place at the flow rate of "zero"). This determination is time-consuming and relatively complicated to implement technically, because the flow velocity must be permanently changed.

The "no-net-flux" protocol represents another possibility for determining the recovery rate and thereby the concentration outside of the catheter. In this connection, different concentrations of the substance to be measured are added to the perfusate. By means of the resulting changes in concentration at the output of the catheter, a conclusion can be drawn with regard to the concentration in the body, i.e. the recovery rate.

All of the calibration methods mentioned until now are not able, however, to determine changing recovery rates during an in vivo measurement. To determine the dynamic recovery rate, a reference substance inherent to the body is therefore also measured, according to the invention. In this connection, it is necessary that the recovery rates for the substance to be determined and for the reference substance are proportional. Due to a concentration difference between the perfusate and the reference substance, a net flow comes about between the reference substance in the catheter and the fluid that surrounds the catheter. This net flow is reflected in a difference in the concentration of the perfusate that flows into and out of the catheter.

The invention therefore takes advantage of the presence of a reference substance in the fluid in which the concentration is supposed to be determined, in other words particularly in the bodily fluid. In medicine, so-called tracers, which are introduced into the body (exogenous reference), are frequently used for this purpose. For scientific studies, it is justifiable to introduce these substances, some of which are harmful (e.g. radioactive). For the development of a system that is to be used routinely by patients, however, it appears to be necessary to use reference substances that already occur in the organism (endogenous reference). For the open microperfusion technique (EP 300 008 B; U.S. Pat. No. 5,193,545 A; U.S. Pat. No. 5,097,834 A), in which direct contact takes place between bodily fluid and perfusate, in contrast to the invention, the osmolarity, impedance, or electrical conductivity is proposed as a measure of the recovery rate.

The present invention, as mentioned, is based on the microdialysis technique for obtaining bodily fluids. In this connection, the recovery rate is preferably determined using the ions that are kept very constant in the body, i.e. the related electrical conductivity or osmolarity, taking into consideration the different diffusion velocities by way of the microdialysis membrane. It is possible to take deposits on the microdialysis membrane itself into consideration by means of determining ions, i.e. the related electrical conductivity, going beyond determination of the recovery rate based on the restricted transport of molecules in the tissue itself, and the exchange process between the bodily fluid and the perfusate. This represents a significant difference from the open microperfusion technique mentioned earlier, in which only the restricted transport in the tissue itself is characterized using osmolarity, impedance, or electrical conductivity, because due to the absence of a membrane, no additional transport barrier exists. In contrast to this, the restricted or changing transport properties by way of the membrane are also taken into consideration in microdialysis, by measuring reference substances.

It is also advantageous, in the technique according to the invention, if any different transport behavior of the reference substance and the substance to be measured is taken into consideration by means of a correction factor that has been determined in advance. In this connection, the said correction factor can be determined in advance, in vitro, in that a solution with ions and the substance to be determined is mixed, and this solution is passed through the membrane or a comparable membrane, e.g. drawn through by suction. However, it is also possible to undertake a parallel measurement of the substance in the blood, in order to determine this correction factor, and to establish a relationship between the measurement value in the blood with the measurement value in the tissue, in order to obtain the correction factor in this manner.

As already mentioned, according to the invention, the measurement of the value to be determined is preferably undertaken on the basis of measuring the electrical conductivity, corresponding to the sum of the ions.

In order to achieve high flow-through rates of the perfusate or the mixture of perfusate/bodily fluid, forced transport using pumping units can be provided. Preferably, in this connection, a pump unit is arranged both in the inflow to the microdialysis catheter and in the outflow from it, and the two pump units are preferably synchronized, in order to guarantee a uniform fluid transport. In order to bring the fluid in question from the catheter to the sensor as quickly as possible, it is practical if the pump unit on the outflow side is arranged behind the sensor unit, viewed in the flow direction. The pump units advantageously can be formed simply by means of peristalsis pumps.

As mentioned, ions are preferably used as the reference value, and if therefore the conductivity is determined in the course of the measuring technique according to the invention, the sensor unit accordingly contains electrodes for determining the conductivity of the fluid that flows through.

The invention will be explained in greater detail below, using preferred exemplary embodiments and making reference to the drawings.

Figure 2:
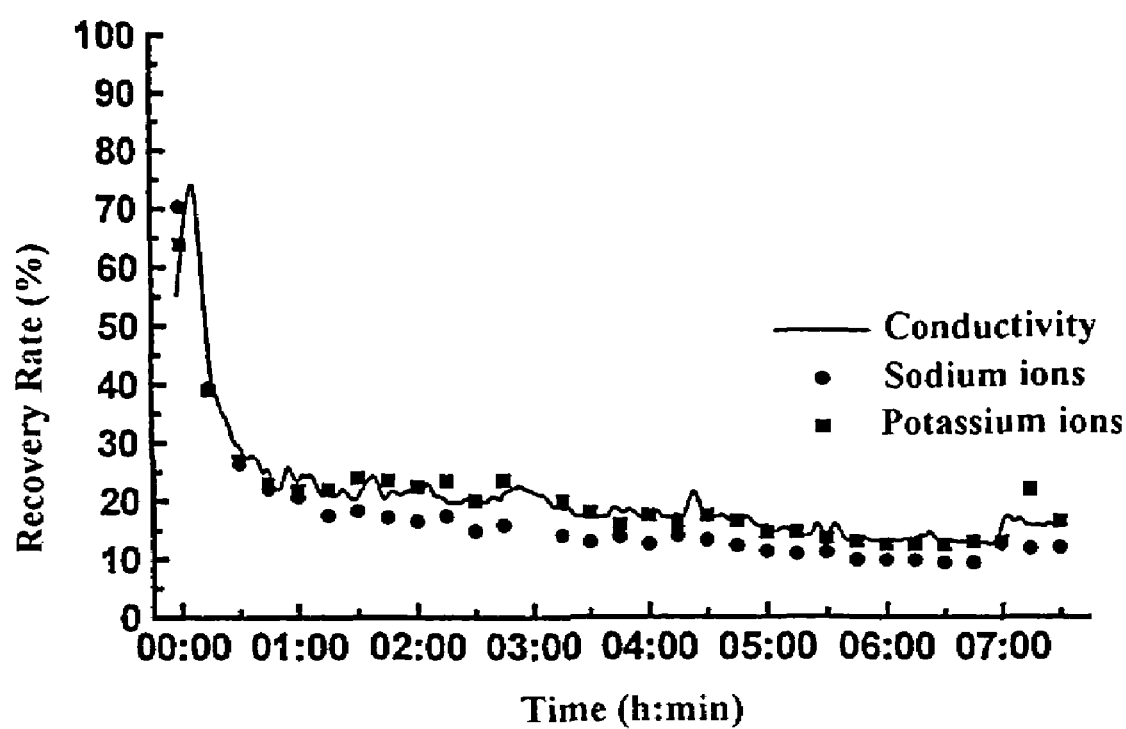
Figure 3:
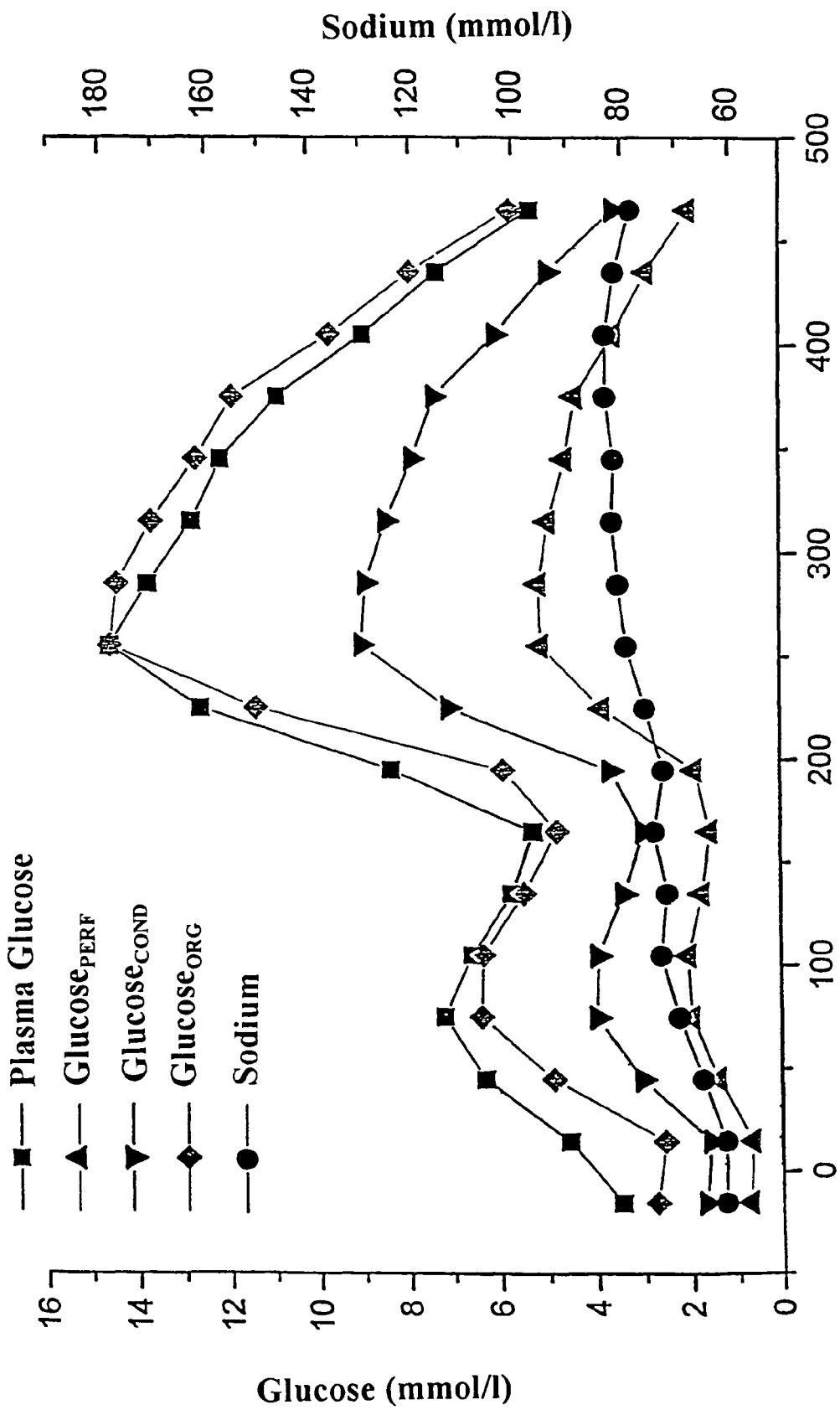
Figure 4:
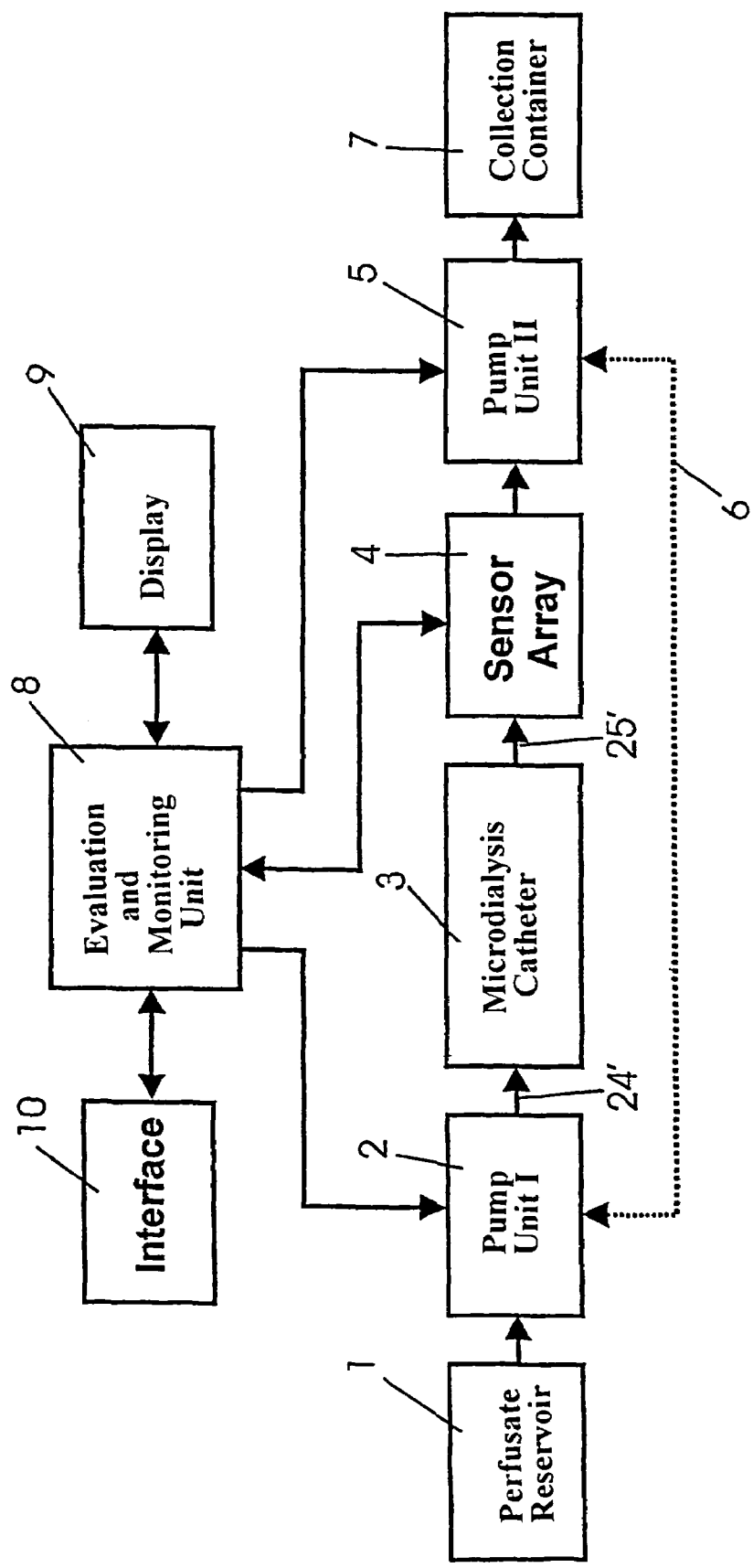
Figure 5:
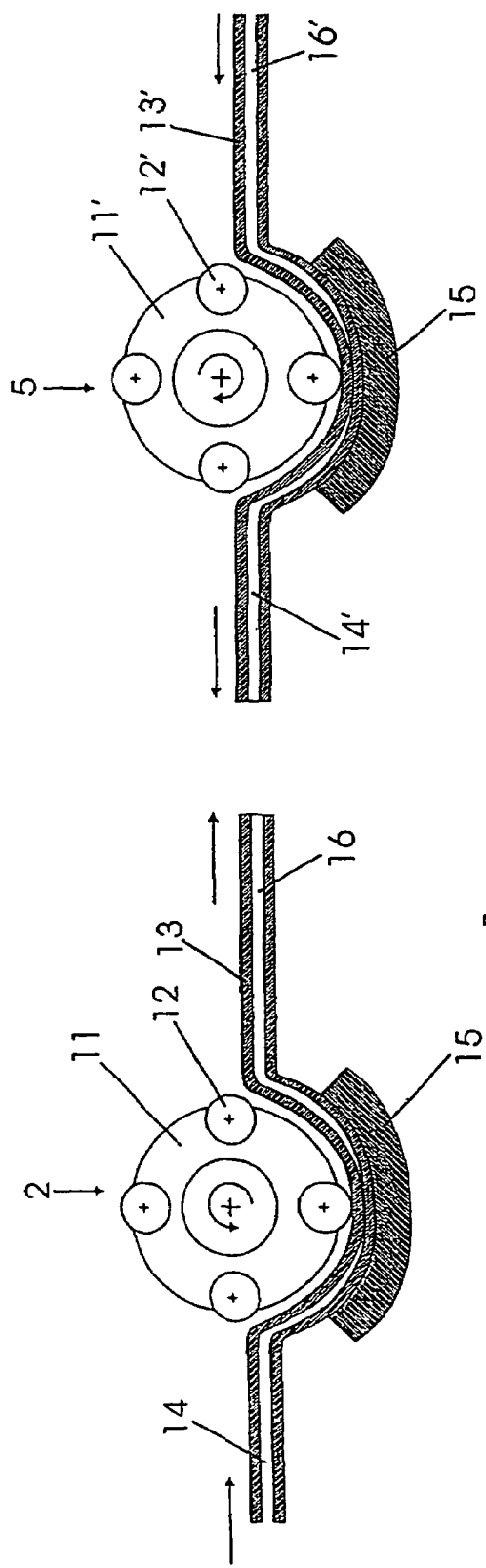
Figure 6:
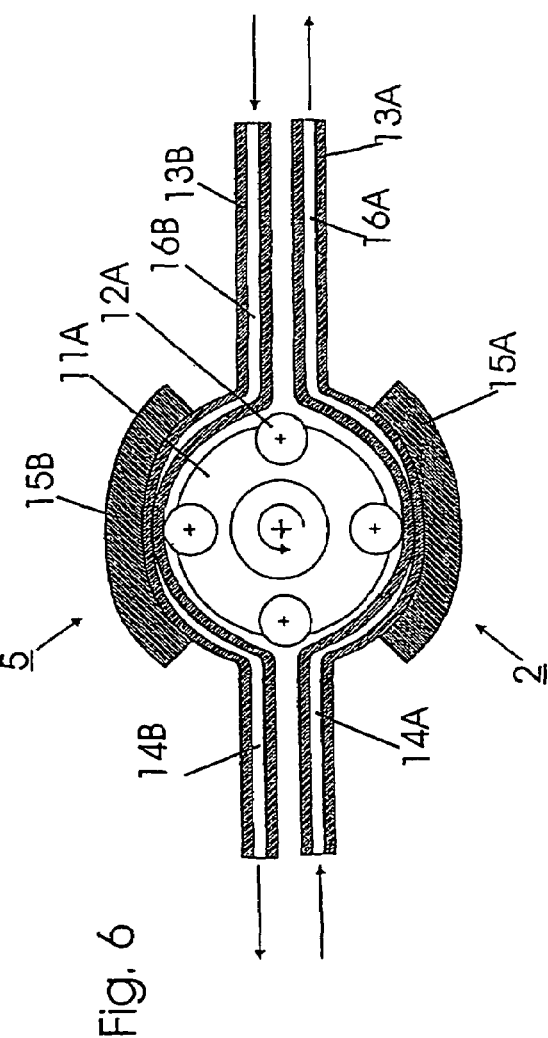
Figure 10:
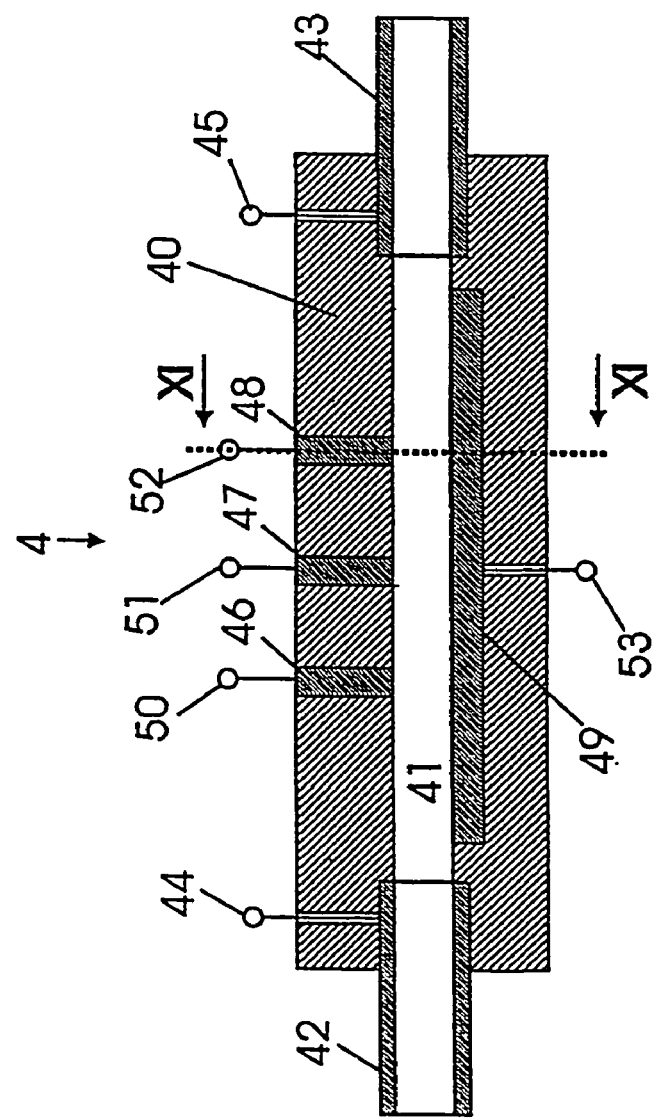
Figure 11:
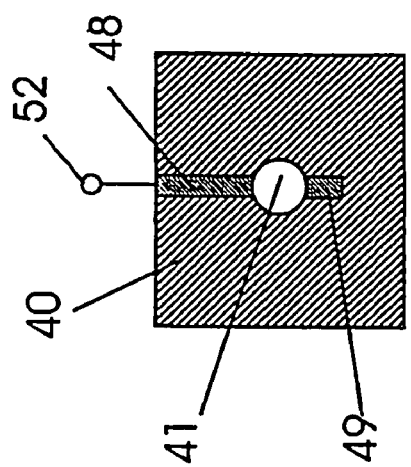

These show:

FIG. 1: schematically, the composition of human tissue fluid, with particular illustration of the cations and anions contained therein;

FIG. 2: a diagram to illustrate the recovery rate of ions and, related to this, the electrical conductivity of a tissue fluid;

FIG. 3: schematically, in a diagram, the concentration progressions of glucose and sodium, proportional to the electrical conductivity;

FIG. 4: in a type of block schematic, a device having a microdialysis catheter to be introduced into a body tissue, for implementation of the measuring method according to the invention;

FIG. 5: a possible embodiment of the pump units used in such a device, in the form of two separate peristalsis pumps;

FIG. 6: a combined peristalsis pump for the formation of the pump units present in the device according to FIG. 4;

FIG. 7: an embodiment of the perfusate reservoir for the device according to FIG. 4;

FIG. 8 and, in an enlarged detail in FIG. 8a: a microdialysis catheter;

FIG. 9: schematically, an embodiment of a collection container for a device according to FIG. 4; and FIGS. 10 and 11: in a schematic lengthwise cross-section and crosswise cross-section, respectively, a sensor unit for the device according to FIG. 4.

As mentioned, the so-called microdialysis technique is used in the present measuring technique for determining the concentration of substances in the living organism, which is known, in and of itself, but was rejected in the past, because of the disadvantage of deposits of substance inherent to the body on the membrane, since the measurement results were therefore considered to be unusable. However, using the proposed technique, a solution is provided, according to which a consideration of the restricted or changing transport characteristics during passage of the bodily fluid through the membrane is taken into consideration on the basis of measuring reference substances.

In detail, an exchange of bodily fluid is made possible by way of this membrane, as is actually known, whereby a so-called perfusate is passed by on the other side of the membrane.

For the characterization of this exchange process, a perfusate that is free of ions, for example, or a perfusate mixed with a defined ion concentration, is used. The change in the ion concentration between the perfusate before and after equilibration with the bodily fluid is a measure of the recovery. In this connection, individual ions can be selectively measured (e.g. sodium or chloride), or preferably the electrical conductivity is measured as the weight sum of all the ion concentrations:

$$\chi = F \cdot \sum |z_i| \cdot c_i \cdot u_i ,  \quad (1)$$

wherein $\chi$ is the electrical conductivity [see original],
F is the Faraday constant [see original],
z is the charge number of the type of ion,
c is the ion concentration [mmol/L], and
u is the ion mobility [see original].

The calculation for determining the substance of interest is based on the following assumptions: The recovery rates (ratio of a substance in the re-perfusate (substance$_{PERF}$) of a catheter to the substance in the organism (substance$_{ORG}$)) for the substance to be determined in the organism substance$_{ORG}$ and the reference substance reference$_{ORG}$ are proportional:

$$\text{Recovery Rate} = \frac{Substance_{PERF}}{Substance_{ORG}} = k \cdot \frac{Reference_{PERF}}{Reference_{ORG}} \quad (2)$$

By transforming this Equation 2, the following equation is obtained for the substance substance$_{ORG}$ to be measured:

$$Substance_{ORG} = Substance_{PERF} \cdot \frac{1}{k} \cdot \frac{Reference_{ORG}}{Reference_{PERF}} \quad (3)$$

| with: | | |
|---|---|---|
| | substance$_{ORG}$ | ... substance to be determined in the organism |
| | substance$_{PERF}$ | ... substance to be determined in the re-perfusate |
| | reference$_{ORG}$ | ... reference substance in the organism |
| | reference$_{PERF}$ | ... reference substance in the re-perfusate |
| | k | ... correction factor for the different recovery rate |

The correction factor k takes into consideration the different transport behavior of the reference substance and the substance to be determined. This correction factor k must be observed when using ions that are charged, and non-charged substances to be measured, by way of a membrane. The determination of this correction factor k, which is newly formed for every substance to be determined, can be determined in different ways. One possibility is, for example, an in vitro determination, in which a solution with ions and the substance to be determined is mixed and collected by way of a microdialysis catheter; the correction factor k can be determined by means of measuring the concentration of ions and the substance to be determined in the dialysate and the known concentrations in the mixed solution. On the other hand, an in vivo determination can also be undertaken. In many areas of medicine, the concentrations in the blood represent the "golden standard," i.e. quantitative knowledge in medicine is generally related to blood. In order to determine the correction factor k, a measurement in the blood can now be undertaken parallel to the measurement in the tissue. By establishing a relationship between the tissue value and the blood value, a correction value $k_o$ is obtained, which now takes not only the correction factor k into consideration, but also possible differences between blood and tissue concentrations, i.e. the factor is no longer determined explicitly, but rather is included in the conversion factor between the blood and tissue concentration.

Determining the concentration of the substance in the organism (substance$_{ORG}$) is based, according to the above Equation (3), on measuring the substance to be determined in the re-perfusate (substance$_{PERF}$), measuring the reference substance in the re-perfusate (reference$_{PERF}$), determining the correction factor for the different recovery rate, and assuming a constant value for the reference substance in the organism (reference$_{ORG}$).

FIG. 1 schematically shows the composition of human tissue fluid with regard to ions. As is evident, the major portion of the ions consists of sodium ions and chloride ions. Because the colloid osmotic pressure is maintained, the concentrations of the electrolytes are maintained within a very small tolerance range, as is the electrical conductivity, which therefore can be used as an endogenous reference.

FIG. 2 graphically shows the recovery rate of ions, namely sodium and potassium ions, as well as, related to this, the electrical conductivity of tissue fluid over time, whereby the ions were obtained using microdialysis. In this connection, it is evident from the diagram of FIG. 2 that the ion concentration can be reproduced by means of the electrical conductivity. Furthermore, it is evident from this human experiment that the recovery rate changes over time; this can be attributable to changes of the membrane permeability (deposits) but also to changes in the transport behavior in the tissue. For a reliable measurement, it is therefore necessary to be able to determine this recovery rate at any point in time during a measurement.

FIG. 3 shows the concentration progressions of glucose and sodium (which is proportional to the electrical conductivity). By measuring sodium and glucose$_{PERF}$ (glucose contained in the perfusate), a calculation back to the glucose$_{COND}$ (glucose concentration corrected by the conductivity) is possible. This glucose$_{COND}$ concentration is furthermore extrapolated by means of a comparison of the plasma glucose with the glucose$_{ORG}$ (glucose in the organism), and is available as a measurement result. The changing sodium concentration (corresponding to the electrical conductivity) must be observed, which reflects a change in the recovery rate and underlines the need for continuously determining this value.

The following table shows the regression between the plasma glucose and the perfusate glucose (substance$_{PERF}$) and the plasma glucose and the tissue glucose (substance$_{ORG}$): $y = A_x + B_x *$perfusate glucose, with $r_x$ ... linear correlation coefficient

| Patient | Perfusate glucose (substance$_{PERF}$) | | | Tissue glucose (substance$_{ORG}$) | | |
|---|---|---|---|---|---|---|
| | $A_1$ | $B_1$ | $r_1$ | $A_2$ | $B_2$ | $r_2$ |
| 1 | −0.44 | 0.412 | 0.875 | 0.979 | 0.769 | 0.962 |
| 2 | 0.174 | 0.312 | 0.886 | 1.039 | 0.606 | 0.963 |
| 3 | −0.879 | 0.43 | 0.961 | −0.971 | 0.708 | 0.974 |
| 4 | 2.776 | 0.237 | 0.769 | 0.489 | 0.702 | 0.992 |
| 5 | 0.284 | 0.217 | 0.654 | −0.165 | 0.651 | 0.952 |
| 6 | 0.833 | 0.19 | 0.716 | −0.647 | 0.672 | 0.962 |

The tissue glucose was determined using the perfusate glucose and ion concentration (proportional to the electrical conductivity). In all the cases, it was possible to significantly improve the correlation between the plasma glucose and the tissue glucose by means of the correction with the conductivity measurement, as can be shown by an increase of the correlation coefficient $r_1$ to $r_2$ barely below 1).

FIG. 4 shows a measurement device according to the microdialysis principle described, in a block schematic. A carrier fluid is pumped into a microdialysis catheter 3 from a perfusate reservoir 1, by way of a first pump unit 2. This carrier fluid flows through the microdialysis catheter 3, thereby partly mixing with bodily fluid, and is subsequently passed to a sensor unit 4. In order to guarantee uniform fluid transport, a second pump unit 5 is located after the microdialysis catheter 3, which is synchronized with the first pump unit 2, as indicated with a broken line in FIG. 4. In this connection, the second pump unit 5 can be positioned before or after the sensor unit 4. In order to keep delays due to the transport from the catheter 3 to the sensor unit 4 as low as possible, it is advantageous if the sensor unit 4 is placed directly after the catheter 3.

The pump units 2, 5 can be structured as individual peristalsis pumps, but it is also possible to affix a pumping hose and a suction hose on the same pump head, see FIGS. 5 and 6 that are explained below. However, the pump units 2, 5 are not restricted to peristalsis pumps, but rather any type of pump (piston pump, partial vacuum containers, excess pressure containers, etc.) is possible.

At the end of the fluid system, the fluid is stored in a collection container 7, according to FIG. 4. An evaluation and monitoring unit 8 coordinates the flow rates of the pumps 2, 5 and controls a display 9 and an interface 10, which serves for the input of operations as well as the output of data.

In FIG. 5, the two pump units 2, 5 are shown as separate peristalsis pumps. These are peristaltic hose squeezing pumps, where rollers 12, 12' are affixed, in each instance, on a pump head 11, 11'. By rotating the pump head 11, 11', the lumen of a related hose 13, 13' is divided into two parts, namely the lumen 14, 14' and the lumen 16, 16'. The hose 13, 13' is squeezed between the rollers 12, 12' and an opposing piece 15, 15', whereby fluid transport, for example from the lumen 14, 14' to the lumen 16, 16', takes place by means of rotating the pump head 11, 11', for example in a counter-clockwise direction. In order to pump and draw fluid synchronously, the two pump units 2, 5 are, however, used in different directions of rotation, as is shown in FIG. 5; the second pump unit 5 is accordingly operated in the clockwise direction.

Another possibility for implementing the two pump units 2, 5 is shown in FIG. 6 and consists of affixing two hoses 13A, 13B to a pump head 11A with rollers 12A and two opposing pieces 15A, 15B. With the prerequisite that the two hoses 13A, 13B and the related opposing pieces 15A, 15B have the same characteristics, absolute synchronicity exists between the two pump devices. The hose lumina that are divided by the pump units 2, 5 are accordingly labeled as 14A, 16A, i.e. 14B, 16B in FIG. 6. Furthermore, the flow direction is indicated in FIG. 6 with arrows, just as in FIG. 5.

A possible embodiment of the perfusate reservoir 1 exists, according to FIG. 7, in the form of a plastic bag 21 having a connection hose 22. Another possible embodiment consists of an ampoule.

According to FIG. 8, the microdialysis catheter 1 consists of a body 23 and two connectors, namely a feed connector 24 and a drain connector 25. Accordingly, in FIG. 8, as in FIG. 4, the inflow to the catheter 3 is indicated, in general, as 24', and the outflow as 25'. The catheter 3 can have a linear structure, comparable to a hose having an input on the one side and an output on the other side, see, for example, U.S. Pat. No. 5,706,806 A, or can also be structured as a double-lumen catheter, as in FIG. 8, see also U.S. Pat. No. 4,694,832 A. In this connection, a membrane 26 encloses a tube 27, thereby forming a lumen 28, as is evident in the detail representation of FIG. 8A, at the catheter tip. Perfusate is introduced into this intermediate space lumen 28 by means of the lumen 29 of the tube 27, whereby the flow direction can also be reversed for the fundamental mode of operation of the catheter 3.

According to FIG. 9, the collection container 7 consists, for example, of a container 30 having a hose connection 31.

A possible embodiment of the sensor unit 4 is shown in FIGS. 10 and 11. A body 40 of the sensor unit 4 has a lumen 41 passing through it, in which the fluid to be analyzed is transported. This sensor body 40 is connected with the related components (e.g. 3 or 5 in FIG. 4) by means of connector pieces 42, 43. These connector pieces 42, 43 can be made of metal, whereby the electrical conductivity can be determined by way of an electrical connection 44, 45 between these connector pieces 42, 43 (axial determination of the conductivity). Another possibility consists of a radial determination of the conductivity, whereby the conductivity is determined between an electrode 46, 47, or 48 and an opposite electrode 49. Actually, only two electrodes are needed to determine the conductivity, e.g. the electrodes 46 and 49, whereby then, the other electrodes 47 and 48 can be used for determining other analytes (e.g. glucose, lactate, etc.). Contact between the electrodes 46, 47, 48 and 49, respectively, is made by way of connectors 50, 51, 52, and 53, respectively.

The invention claimed is:

1. Method for measuring the concentration of substances in living organisms using microdialysis, wherein bodily fluid is mixed with a perfusate and passed through a membrane, and a substance concentration of the bodily fluid is determined using a sensor unit, characterized in that in order to take into consideration the restricted transport of the substance through the membrane, so that the measured substance concentration differs from the actual substance concentration in the organism, an endogenous substance used as a reference substance, having a known value, is measured after passing through the membrane and mixing with the perfusate, and the actual substance concentration is determined on the basis of the quotient of the known reference substance value divided by the measured reference substance value, multiplied by the measured substance concentration.

2. Method according to claim 1, characterized in that any different transport behavior of the reference substance and the substance to be measured is taken into consideration by means of a correction factor that is determined in advance.

3. Method according to claim 2, characterized in that the correction factor is determined in advance, in vitro, by mixing a solution with ions and the substance to be determined, and passing it through a membrane.

4. Method according to claim 2, characterized in that the correction factor is determined in advance, in vivo, by measuring the substance value in the blood.

5. Method according to claim 1, characterized in that the measurement of the value to be determined is performed on the basis of measuring the electrical conductivity, corresponding to the sum of ions.

6. Method according to claim 1, characterized in that in order to achieve high flow-through rates, the perfusate or the mixture of perfusate/bodily fluid is pumped into and out of the body.

7. Device for measuring the concentration of substances in living organisms using microdialysis, having a microdialysis catheter that has a membrane, through which bodily fluid is mixed with a perfusate that is supplied from a perfusate reservoir, and having a sensor unit for determining the substance concentration of the bodily fluid, characterized in that the membrane is also set up for passage of an endogenous substance used as a reference substance, having a known value, and this reference substance is measured after passing through the membrane and mixing with the perfusate, using the sensor unit, and that the sensor unit is connected with an electronic evaluation unit, which is set up to determine the actual substance concentration on the basis of the quotient of the known reference substance value divided by the measured reference substance value, multiplied by the measured substance concentration.

8. Device according to claim 7, wherein a first pump unit is arranged on the inflow side of the microdialysis catheter, and a second pump unit is arrancred on the outflow side of the microdialysis catheter.

9. Device according to claim 8, wherein the first and the second pump units are synchronized.

10. Device according to claim 8, wherein the second pump unit on the outflow side is arranged behind the sensor unit, viewed in the flow direction.

11. Device according to claim 8, wherein the first and second pump units are peristalsis pumps.

12. Device according to claim 7, wherein the sensor unit has electrodes for determining the conductivity of the fluid that flows through.

* * * * *